(12) United States Patent
Dreher

(10) Patent No.: US 9,668,895 B2
(45) Date of Patent: Jun. 6, 2017

(54) BENDABLE STENT

(71) Applicant: C. R. Bard, Inc., Tempe, AZ (US)

(72) Inventor: Gael Dreher, Karlsruhe (DE)

(73) Assignee: C.R. Bard, Inc., Murray Hill, NJ (US)

(*) Notice: Subject to any disclaimer, the term of this patent is extended or adjusted under 35 U.S.C. 154(b) by 96 days.

(21) Appl. No.: 14/728,981

(22) Filed: Jun. 2, 2015

(65) Prior Publication Data

US 2015/0257909 A1 Sep. 17, 2015

Related U.S. Application Data

(60) Division of application No. 13/975,147, filed on Aug. 23, 2013, now Pat. No. 9,050,203, which is a continuation of application No. 12/594,531, filed as application No. PCT/EP2008/054007 on Apr. 3, 2008, now Pat. No. 8,518,101.

(30) Foreign Application Priority Data

Apr. 3, 2007 (GB) .................................. 0706499.1

(51) Int. Cl.
*A61F 2/89* (2013.01)
*A61F 2/91* (2013.01)
*A61F 2/915* (2013.01)

(52) U.S. Cl.
CPC .................. *A61F 2/89* (2013.01); *A61F 2/91* (2013.01); *A61F 2/915* (2013.01); *A61F 2002/91508* (2013.01); *A61F 2002/91533* (2013.01); *A61F 2002/91558* (2013.01); *A61F 2230/0054* (2013.01)

(58) Field of Classification Search
CPC ............. A61F 2002/91508; A61F 2002/91558
USPC ........................................... 623/1.15–2, 1.22
See application file for complete search history.

(56) References Cited

U.S. PATENT DOCUMENTS

| 7,204,848 | B1* | 4/2007 | Brown ...................... A61F 2/91 623/1.15 |
| 2004/0073291 | A1* | 4/2004 | Brown ...................... A61F 2/91 623/1.15 |
| 2007/0250148 | A1* | 10/2007 | Perry, Jr. ................... A61F 2/91 623/1.11 |

* cited by examiner

*Primary Examiner* — Sarah W Aleman
(74) *Attorney, Agent, or Firm* — C.R. Bard Intellectual Property

(57) ABSTRACT

A stent formed by slitting a tube to create a matrix of struts, the slitted tube being radially expandable to a stenting disposition in which the struts exhibit a zig-zag pattern in successive loops around the circumference of the stent, the zig-zag pattern exhibiting a cusp between any two adjacent struts, with selected tied cusps of any one loop being connected by a bridge to a facing cusp of the adjacent loop and with intervening free cusps, characterized by lengthwise staggering of circumferentially adjacent said slits within said loops, wherein any two struts that are contiguous with a said tied cusp are of different lengths and any strut that extends from one free cusp to another free cusp has the same length as any other such strut such that, in the said stenting disposition, the free cusps of adjacent loops are circumferentially displaced from each other.

19 Claims, 5 Drawing Sheets

BENDABLE STENT

PRIORITY

This application is a divisional of U.S. patent application Ser. No. 13/975,147, filed Aug. 23, 2013, now U.S. Pat. No. 9,050,203, which is a continuation of U.S. patent application Ser. No. 12/594,531, filed Dec. 7, 2009, now U.S. Pat. No. 8,518,101, which is a U.S. national stage application under 35 USC §371 of International Application No. PCT/EP2008/054007, filed Apr. 3, 2008, claiming priority to United Kingdom Patent Application No. 0706499.1, filed Apr. 3, 2007, each of which is incorporated by reference in its entirety into this application.

FIELD OF THE INVENTION

This invention relates to radially expansible stents for transluminal delivery to a stenting site within the body of a patient, the stent having an enhanced capacity for bending, after deployment in the body.

There are some stenting sites within the body in which there is substantial deformation of the lumen that is stented. Consider, for example, a peripheral vascular stent at a site near the knee. When an expanded stent suffers severe bending, there can be buckling on the inside of the bend. Even before there is any catastrophic buckling, the likelihood exists that portions of the stent matrix, spaced apart along the axis of the stent lumen, will approach each other and impact, on the inside of any temporary tight bend, to the detriment not only of the tissue caught between the impacting portions of the stent, but also the stent matrix itself. It is an object to the present invention to ameliorate this problem.

BACKGROUND OF THE INVENTION

The present applicant is a specialist in the manufacture of stents of nickel-titanium shape memory alloy, manufactured from a raw material that is a tubular workpiece of that alloy. To make the stent matrix, the alloy tube workpiece is subjected to a laser-cutting step in which the laser cuts a multiplicity of slits in the tubular workpiece. Each slit extends through the entire wall thickness of the tube, and for the most part, the slits all have the same length and are all parallel to the longitudinal axis of the tubular workpiece. When one advances around the circumference of the tubular workpiece, crossing transversely over a multiplicity of the slits, one by one, alternate slits that one crosses are staggered, in the axial direction of the tube, by a distance that is around half the length of each slit. When such a slitted tube is slipped over a mandrel, and expanded radially, each slit opens out into a diamond-shaped aperture in the wall thickness of the tube. Looked at in another way, the creation of the slits at the same time creates struts of material that lie between adjacent slits, and the struts in the radially expanded tube emerge as zig-zag stenting rings with a characteristic strut length within any one zig-zag ring that is more or less half the length of each of the slits cut by the laser.

Where two struts, next adjacent within the circumference of a zig-zag ring, come together, we can call this a "cusp". The cusps of each zig-zag ring are contiguous with cusps of the next adjacent stenting ring.

For enhanced flexibility of the zig-zag stent matrix, many of the "connector portions" between facing cusps of adjacent zig-zag stenting rings can be parted, to leave only a few (typically four or less) connector bridges between any two axially adjacent zig-zag stenting rings. See our WO 94117754. The surviving connector bridges have a length direction parallel to the longitudinal axis of the stent matrix.

However where these connector bridges have been removed, there are still cusps of adjacent zig-zag stenting rings that are effectively "head to head" across the narrow gap with a cusp belonging to the adjacent zig-zag ring. When such a narrow gap is on the inside of the bend, upon bending the expanded stent (by movement of the body after the stent has been placed in the body), there is the likelihood of the two cusps head to head impacting on each other. It is common to call this "peak to peak".

In this discussion, it is important to distinguish between the radially compact trans-luminal delivery disposition of the stent matrix (not very different from the as-cut disposition of the stent matrix, before expansion on the mandrel to diamond-shaped apertures) and the radially expanded and deployed configuration of the stent, where the struts form zig-zag rings. A head to head facing configuration of parted connector portion cusps is tolerable for the delivery procedure but to be avoided, if that is feasible, after stent deployment and radial expansion.

The present applicant has been interested in this objective for some years. For a previous proposal for improvements see its WO 01176508/published Oct. 18, 2001. The present invention represents a fresh approach to the problem and, it is thought, a more elegant solution.

Other makers of stents have concerned themselves with the same objective. See for example US 2004/0073290 A1 where (paragraph 0002) it is explained that "if adjacent rings are spaced too close together" then "interference can occur between adjacent rings on the inside of a bend". Clearly, the idea of spacing the axially adjacent rings further apart has limited appeal/because it leaves the space between the rings unstented.

Self-expanding stents of nickel-titanium shape memory alloy are not particularly radiopaque and so are often equipped with radiopaque markers, of which one favored material is tantalum because it is close to the nickel-titanium alloy in electrochemical potential/thereby minimizing galvanic corrosion in the electrolyte of a bodily fluid.

Self-expanding stents are usually deployed by proximal withdrawal of a sheath of a catheter delivery system. To prevent the stent moving proximally with the withdrawing sheath it is conventional to use a pushing annulus that abuts the proximal end zone of the stent and resists any proximal movement of the stent relative to the stent delivery catheter as such. As stent performance and length go up so does the compressive stress imposed on the end zone of the stent by the pushing annulus during withdrawal. It is important to avoid imposing on any part of the end zone a magnitude of stress higher than that of the design performance limits for that stent. The present inventor knows that one way to manage that peak stress is to build the stent so that the end zone has all its cusps touching a notional circle transverse to the longitudinal axis of the stent, so that the stress from the pushing annulus is shared equally amongst all those cusps. For an example of a stent with such an end zone, see WO 2006/047977.

EP-A-1767240 offers ways to increase the flexibility of a stent in its radially compact delivery disposition. It suggests resorting to portions not parallel to the stent length, such as struts that are curved, or bridges that are skewed to the long axis of the stent.

SUMMARY OF THE INVENTION

The present invention is defined in the claims below in which different aspects are presented in respective independent claims, and dependent claims are directed to optional or preferred features. In one embodiment, the invention takes the form of a laser-cut stent in which the slits cut by the laser in the tubular workpiece that is the precursor of the stent are staggered with respect to each other, in the length direction of the stent cylinder such that the slits cut by the laser are, in general, all the same length but the struts created by cutting the laser slits are not all the same length because the axial stagger between circumferentially adjacent slits is arranged to be something other than half the common slit length. However, as the accompanying drawings will reveal, even when many of the slits can be made free of axial displacement (staggering) relative to the circumferentially next adjacent slits, the effect of eliminating head to head cusps on adjacent stenting rings can still be accomplished. As long as some of the adjacent slits are staggered, by an amount other than a one half slit length, the necessary circumferential displacement of facing cusps away from each other can still be achieved, as the slitted tube undergoes radial expansion.

DETAILED DESCRIPTION

Figure 1:
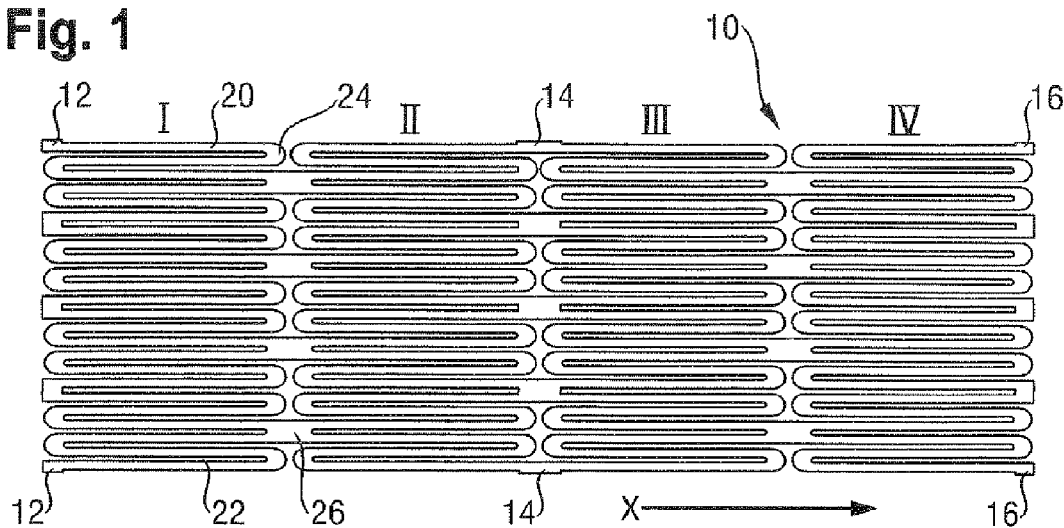
FIG. 1 is a view from above, of a slitted tube opened out flat

Referring to FIG. 1, we see a slitted tube 10, opened out flat by parting the slitted tube at interface portions 12, 14 and 16 to display, opened out flat, a succession of stenting rings I, II, III, IV arranged next to each other along the length of the slitted tube parallel to its long axis direction X. Each of the four stenting rings exhibits a serial progression of nt struts, here 24 struts, (20) separated from each other by the slits through the wall thickness of the tubular workpiece, the succeeding struts of each stenting ring being joined by successive cusps 24. In the unexpanded slitted configuration of FIG. 1, each cusp is in "head-to-head" relationship, along the axis direction X of the slitted tube, with a cusp of the adjacent stenting ring. As can be seen, each stenting ring is connected to the next adjacent stenting ring by four bridges 26 distributed at regular intervals (90°) around the circumference of the slitted tube. The number of bridges per n ring is $n_b$ and the number of struts between successive bridges is $n_s$ so: $n_t = n_s \cdot n_b$.

In stent technology, particularly stents made of shape memory alloy (NITINOL), a strut matrix made by slitting a precursor tube is conventional.

Figure 2:
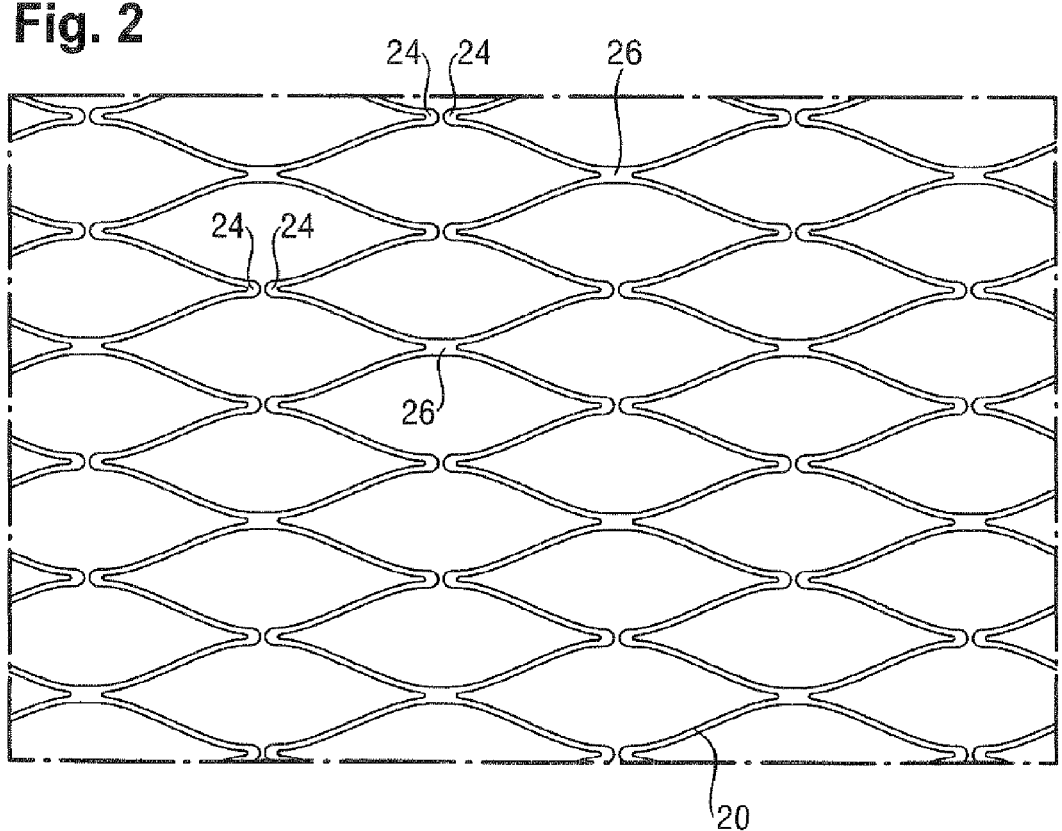
FIG. 2 shows a portion of the matrix of FIG. 1, radially expanded (but also opened out flat)

Turning to FIG. 2, we see a portion of the FIG. 1 slitted tube radially expanded so that the struts of each stenting ring are inclined to the axial direction X and present themselves as a zig-zag sequence of struts around the circumference of the stent. It will be noted that the cusps 24 of adjacent stenting rings are still in head-to-head disposition. Skilled readers will appreciate that any gross bending of a deployed stent is liable to bring opposing cusps on the inside of the bend into physical contact with each other.

Figure 3:
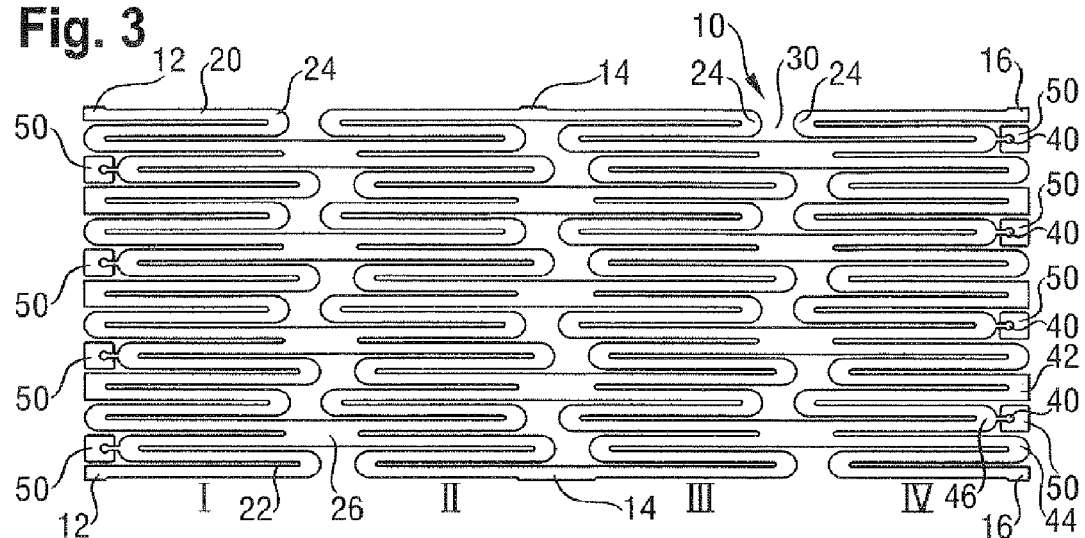
FIG. 3 shows another embodiment of slitted tube opened out flat.

Turning to FIG. 3, we can recognize the same pattern of 24 struts 20 making up 4 adjacent stenting rings I, II, III, IV, recognizably equivalent to what is shown in FIG. 1. Further, just as in FIG. 1, each cusp 24 is in head-to-head relationship with a cusp of the next adjacent stenting ring. Just as in FIG. 1, each stenting ring is connected to the next adjacent stenting ring by four bridges 26.

However, the slits 22 in the tube 10 that have created the strut matrix are axially staggered relative to each other, in a way which is not present in drawing FIG. 1. In consequence of this axial staggering, there is also axial staggering of the gaps 30 between each pair of facing cusps 24. In FIG. 3, there is shown a greater axial separation between facing cusps 24 than is apparent from FIG. 1, but this is not the decisive difference between the FIG. 1 concept and that of FIG. 3.

Reverting to FIG. 1, and concentrating on a pair of struts defining between them an individual gap 22, one can see that the axial length of the two struts, one each side of the slit 22 1 is the same. However, when we look at FIG. 3, and a particular slit 22, we notice that the length of the strut that extends down each side of the slit 22, from the common cusp 24 at one end of the slit, are different. This has repercussions for the way the struts deform when the slitted tube of FIG. 3 is radially expanded, to the zig-zag pattern shown in FIG. 4.

Figure 4:
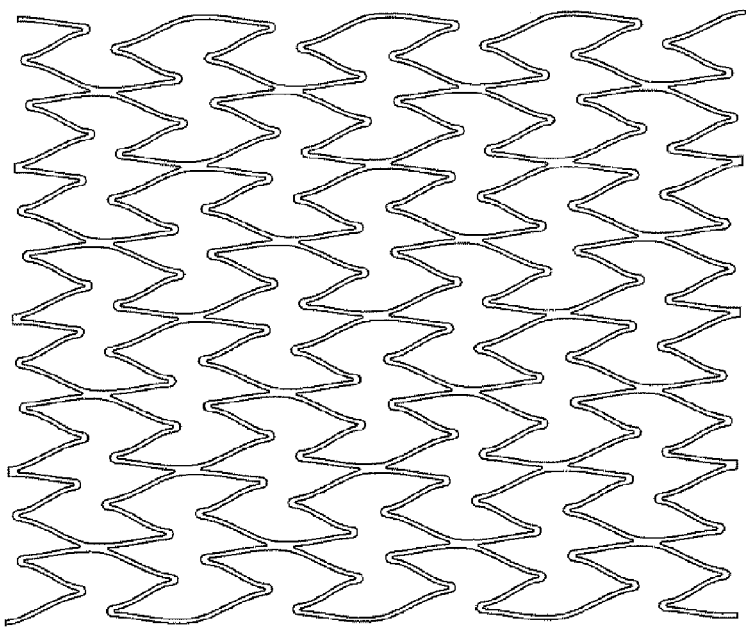
FIG. 4 shows the FIG. 3 strut matrix, opened out flat, and expanded.

Comparing FIG. 4 with FIG. 2, it is immediately evident that there are no longer pairs of cusps 24 facing each other, head to head. Instead, each cusp points towards a gap between two adjacent cusps of the adjacent zig-zag stenting ring. The skilled reader will appreciate that when the stent of FIG. 4 is bent (into a banana shape) each cusp is free to advance axially into the gap between two adjacent cusps of the adjacent stenting ring, rather than striking, head on, the facing cusp of the adjacent stenting ring, as in FIG. 2.

Figure 5:
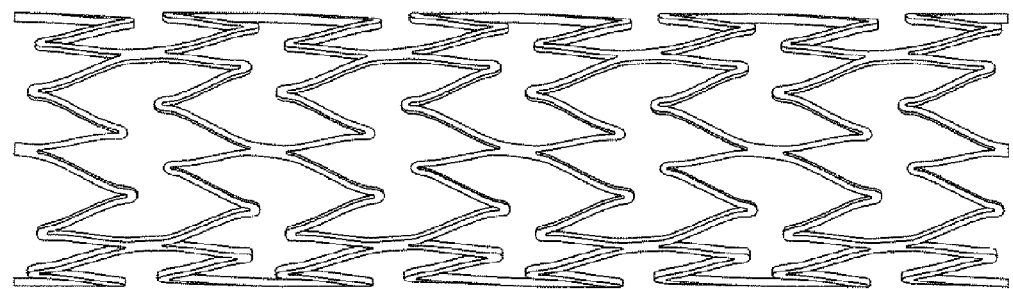
FIG. 5 is a perspective view of the FIG. 4 strut matrix, not opened out flat

FIG. 5 is a perspective view but shows the same phenomenon as is drawn in drawing FIG. 4 with the same strut matrix.

Figure 9:
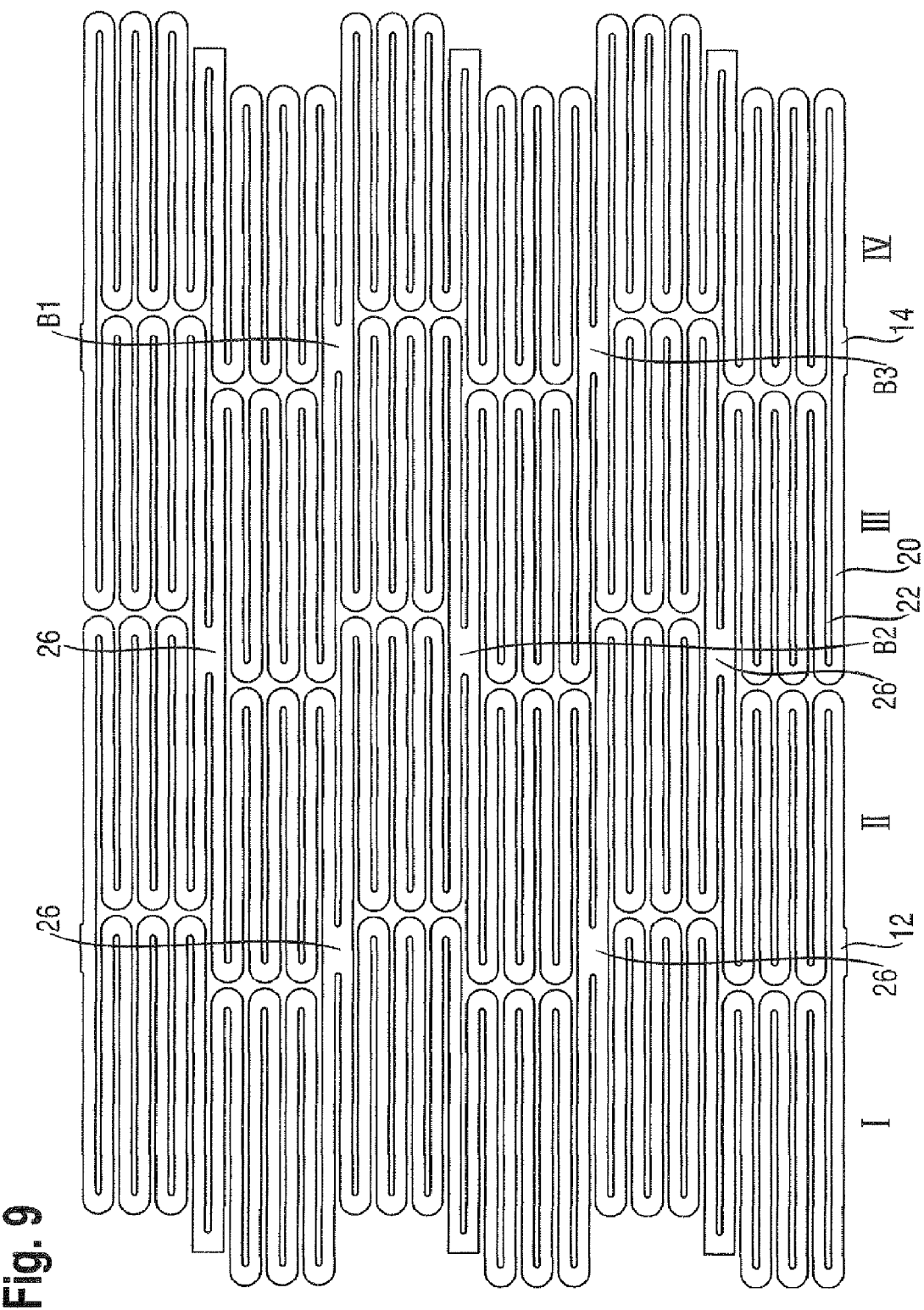
FIG. 9 is a view from above, like that of FIGS. 1, 3 and 6 but of yet another embodiment of a slitted tube opened out flat.

The skilled reader will grasp that the number of struts in each stenting ring need not be 24, and the number of bridges between adjacent stenting rings need not be four. Another arrangement that shows promise is one in which each stenting ring has 42 struts and adjacent stenting rings are connected by three bridges distributed at 120° intervals. Such an arrangement is shown in FIG. 9 and is described below.

Figure 6:
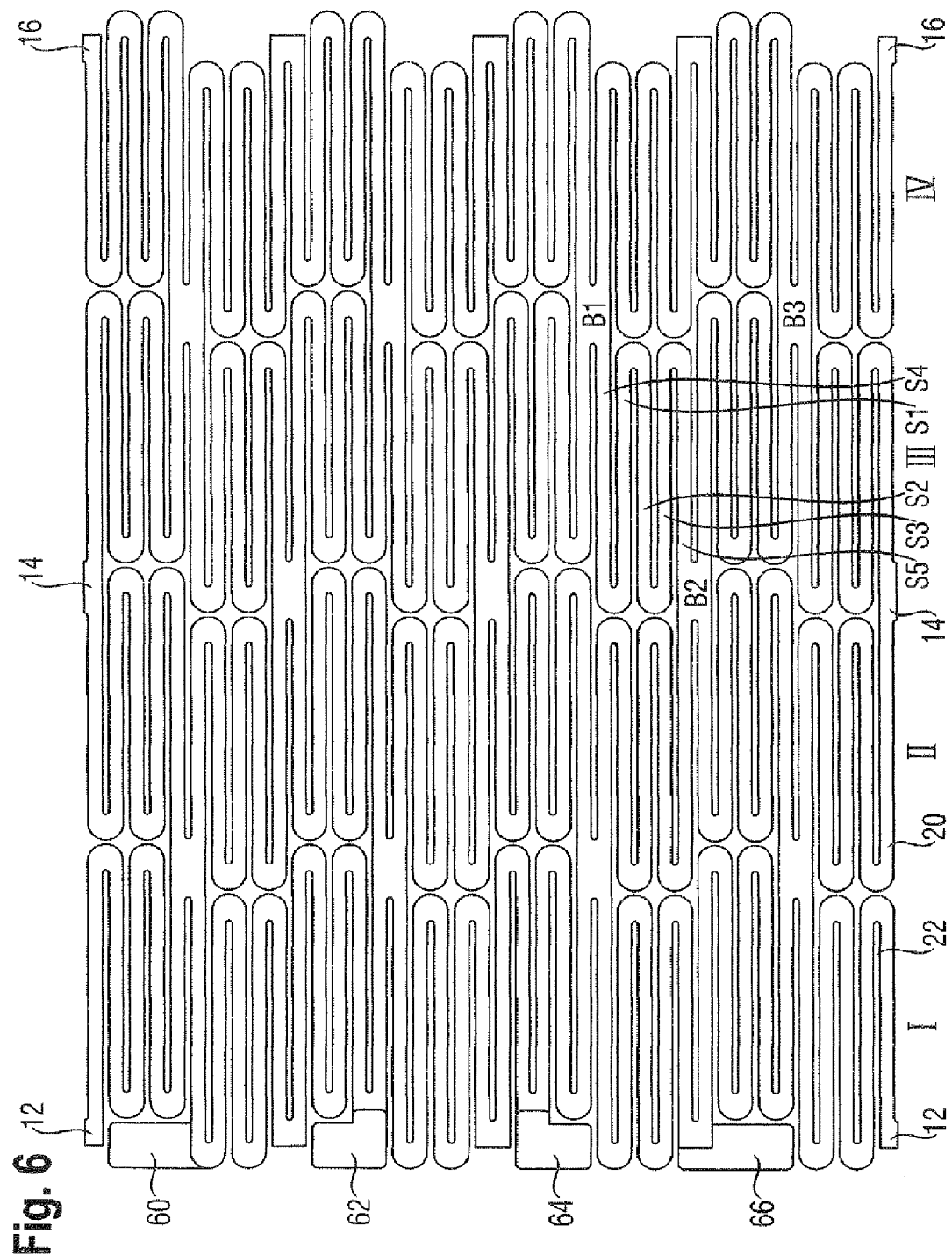
FIG. 6 is a view of another slitted tube opened out flat.
Figure 7:
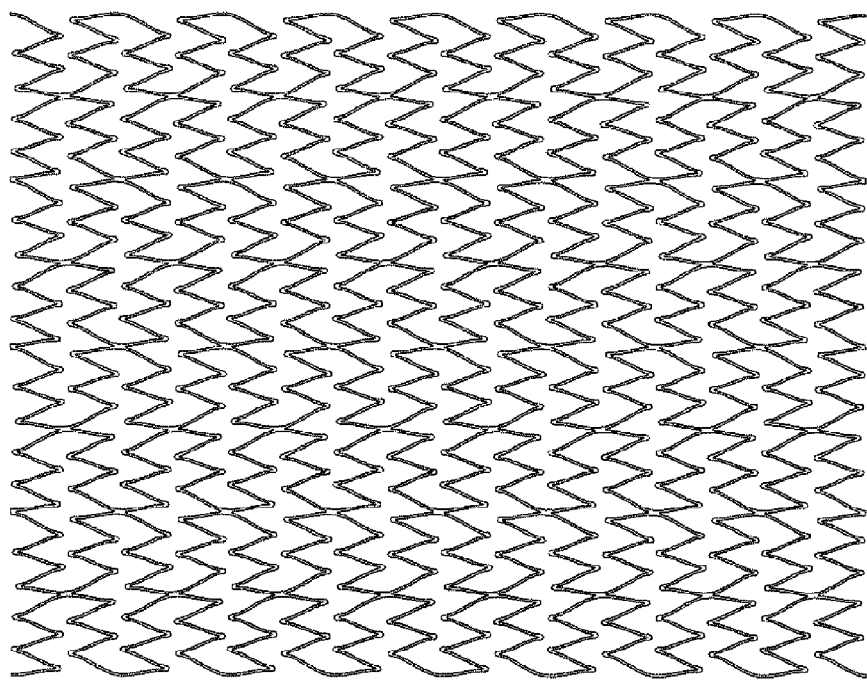
FIG. 7 is a view of the slitted tube of FIG. 6, radially expanded and opened out flat
Figure 8:
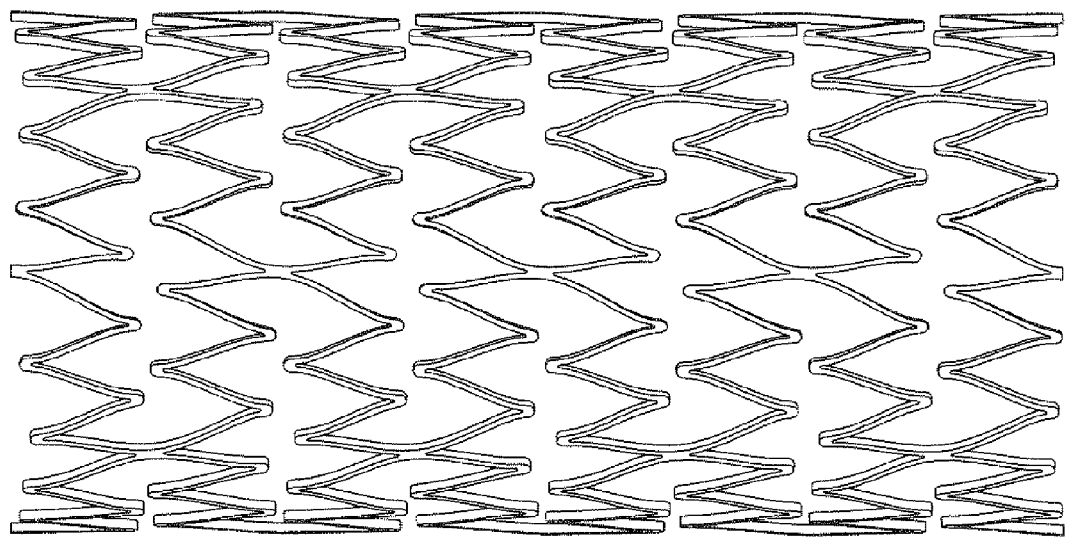
FIG. 8 is a perspective view of the radially expanded tube of FIGS. 6 and 7.

FIGS. 6, 7 and 8 show another attractive design, namely, a slitted tube with 40 struts per ring and four bridges. Since other aspects of the design are described above with reference to FIGS. 3 and 4, the same reference numbers are used to identify corresponding features of the design. Again, it can be seen that when the FIG. 6 slitted tube is opened out radially, the cusps 24 automatically move to positions where they are no longer facing head to head any cusp of the adjacent zig-zag stenting ring, with consequential advantages of avoiding cusp to cusp contact when the deployed stent is subjected to bending deformation.

In FIG. 6, in loop III, three successive bridges are labeled B1, B2, B3. Bridges B1 and B3 connect loop III to loop IV. Bridge B2 is one of the four bridges that connect loop III.

Between bridges B1 and B2, and between bridge B2 and B3, is a sequence of five struts. Three of these struts S1, S2, S3, have the same length. Each extends between two free cusps. The other two struts, S4 and S5, have lengths different from each other. This length difference is what takes the free cusps of adjacent loops out of a head-to-head facing relationship in the expanded configuration of the stent, as can be understood from FIGS. 7 and 8, which also reveal that the bridges are correspondingly skewed, relative to the long axis of the stent, in the expanded disposition of the stent.

The lengthwise staggering of cusps that characterizes the present invention can deliver useful technical effects that include the following.

When a self-expanding strut is to be released from its catheter delivery system, the usual way is to withdraw proximally, relative to the stent, a restraining sheath that surrounds its abluminal surface. When all cusps in a loop are at the same point along the axis of the stent, all can spring radially outwardly from the sheath simultaneously. This impulsive release is not ideal for controlled release. Axial staggering of cusps can assist in releasing the stent more progressively and steadily, cusps escaping one by one from the inward radial confinement of the proximally retreating sheath.

For some stents, the design features non-identical proximal and distal ends, so that it is critically important to load the stent in the delivery system with its distal end nearer the distal end of the delivery system. An advantage of the present invention is that it permits the building of stents with identical distal and proximal ends, that are indifferent to the choice of stent end to lie closer to the distal end of the delivery system.

The axial staggering opens up possibilities for "recesses" such as recesses 40 in FIG. 3, where radiopaque marker elements 50 can be located. These elements thus lie snug between circumferentially spaced apart cusps 42, 44 and axially adjacent to intervening cusps 46, to which it will be convenient to attach the marker. Any axial pushing on the stent, while the confining sleeve is withdrawn is customarily applied to the end surface of the stent. By locating markers in the end recesses and arranging for the end elevation of the stent to comprise both cusps and markers, the stresses on the end elevation are distributed around the circumference as evenly as possible, and over the maximum area of surface of the implant, which is good for fatigue performance, quality control, and efficiency of stent release. Finally, with markers recessed into the end zone of a stent, the markers when imaged give a true impression of where the stent matrix is, and where it is not. A short look at US 2006/0025847 serves to reveal the advantages of the present proposal over another recent proposal to deal with pushing forces.

Not to be underestimated is the advantage yielded by this invention, that a "peak-to-valley" distribution of cusps in the expanded deployed disposition is automatic, regardless how short are the bridges between adjacent stenting loops. Short, strong, robust bridges that connect axially adjacent stenting loops are greatly to be welcomed, for many reasons. In particular/they are less vulnerable to inadvertent straining (bad for fatigue performance if nothing else) when stent matrices are being installed in a catheter delivery system, or when being deployed out of one. Put another way, the stent with short stubby bridges can be rated for greater loads imposed on it during loading or deployment. Since the radial force that a stent can exert on surrounding bodily tissue increases with the number of stenting loops per unit (axial) length of the stent, a reduction in the length of the bridges connecting axially adjacent stenting loops will give rise to an increased stenting force.

However, short stubby bridges are disadvantageous, to the extent that they prejudice stent flexibility. The more flexible a stent is, the better its resistance to fatigue failure (other things being equal). One way to deliver more flexibility, despite an absence of much flexibility in the bridges, is to increase the number of struts in the sequence of struts between each bridge and the next bridge. On that basis, the arrangement of FIG. 9, with 7 struts between any two bridges B1, B2 or B2, B3, is superior to the FIG. 6 design with 5 struts, itself superior to that of FIG. 3, with 3 struts.

When it comes to radiopaque markers, it is important to arrange the markers so that they are distributed around the circumference of the stent, in the radially compact delivery disposition of the stent, as evenly as is practicable. In FIG. 3, the arrangement is even. FIG. 6 shows one possible arrangement of tantalum markers 60, 62, 64, 66 which is not far from an even distribution in the compact form of the stent (although further from evenly distributed when the stent is expanded). In the FIG. 9 design it is clear that each end of the stent offers only three recesses for installation of a set of three markers evenly distributed around the circumference of the stent.

The markers can be of different shapes, in order to meet these design objectives, as is illustrated in FIG. 6, as one example.

One thing that is striking about the present invention is how it delivers a simple pattern of linear slits in the compact configuration that exhibits in each stenting loop a sequence of stepwise displacements, up and down the axis of the stent, in the positions of the free cusps, yet, in the expanded disposition of the stent, the axial steps are gone. Instead, the bridges are skewed, and the free cusps are circumferentially displaced, relative to the free cusps of the adjacent stenting loop that were facing them, head-to-head, in the compact disposition. Of significance is that, in the expanded disposition, when the stent must exert radially outward stenting force on the bodily tissue that forms the wall of the stented bodily lumen, the zig-zag struts of each stenting rings march around the circumference of the lumen in a progression in which axial displacement of free cusps, relative to each other, is difficult to discern. Instead, the stenting loops deploys in a way that is close to an optimal planar hoop, transverse t the axis, for generating a large mechanical radially outward stenting force.

Applicant's WO 2007/135090 discloses a stent that is "bend-capable" in that cusps move out of a "head-to-head" facing relationship in the expanded deployed stent, when the stent tube is bent out of a straight configuration. It will be apparent to the skilled reader that the present invention (lengthwise staggering of cusps) can be combined with the invention of WO2007/135090 (skewed unit cell) to deliver a stent matrix that avoids a head to head facing relationship of cusps, regardless of the extent to which the stent is bent out of a straight line after deployment. One way to accomplish the result explained in WO 20071135090 is to arrange the strut matrix such that $n_s/2$ is an even number.

It hardly needs to be added, that the stents taught in this disclosure can be used in the same way as prior art stents are used. They can carry graft material, or drugs, for example. They can be delivered transluminally, by a suitable catheter delivery system. They can carry radiopaque markers, as is taught in the state of the art. They will find particular application in situations where the stent, after deployment, is subject to a high degree of bending.

The present drawings show specific embodiments which are to be assessed as exemplary, not limiting. The stent need not be made from shape memory metal and need not be laser cut. The inventive concept disclosed herein is applicable to a wide range of known stent technologies.

What is claimed is:

1. A stent having a proximal end and distal end, the stent comprising:
 a strut arrangement having expanded and non-expanded states;
 the strut arrangement forming a plurality of loops along a stent longitudinal axis;
 the loops comprise
  tied cusps connecting adjacent tied struts and bridging to tied cusps on adjacent loops;
  and
  free cusps connecting adjacent free struts,
 wherein
  adjacent tied struts have different lengths,
  a free cusp in each loop connects adjacent, approximately equal-length free struts,
  and
  the stent exhibits a rotational symmetry about an axis perpendicular to the stent longitudinal axis and through the center of the stent such that the strut arrangement is identical from the proximal end to the distal end as from the distal end to the proximal end.

2. The stent of claim 1 wherein not all of the free cusps on adjacent loops align.

3. The stent of claim 2 wherein each loop includes either 24, 40, or 42 struts.

4. The stent of claim 3 wherein
 four or more free cusps are disposed on both a first loop and a second loop between any two bridges connecting the first loop to the second loop,
 and
 in the non-expanded state, two or more gaps formed between facing cusps of the at least four free cusps align and at least two gaps formed between facing cusps of the at least four free cusps skew.

5. The stent of claim 4 wherein a plurality of radiopaque markers are distributed around a circumference of the stent, each of the radiopaque markers positioned in a recess defined between outer surfaces of adjacent end cusps.

6. The stent of claim 5 wherein the plurality of radiopaque markers are spaced axially apart from an intervening cusp between the adjacent end cusps.

7. The stent of claim 6 wherein radiopaque markers in an end zone of the stent are evenly spaced around the circumference when the stent is in the non-expanded state.

8. The stent of claim 7 wherein two or more radiopaque markers have different shapes.

9. The stent of claim 8 wherein three or more of the radiopaque markers each have a different shape.

10. The stent of claim 9 wherein the plurality of radiopaque markers and the end cusps each touch a notional circle transverse to a longitudinal axis of the stent, wherein stress imposed on the stent by a pushing annulus is shared amongst all of the end cusps and all of the plurality of radiopaque markers.

11. The stent of claim 3 wherein the stent includes:
 42 struts in each loop;
 3 bridges connecting any two loops;
 and
 five or more, consecutive, approximately equal-length struts located between adjacent bridges.

12. The stent of claim 3 wherein the stent includes:
 40 struts in each loop;
 4 bridges connecting each pair of adjacent loops;
 and
 three or more, consecutive, approximately equal-length struts located between adjacent bridges.

13. The stent of claim 1 wherein the bridges between any two adjacent loops are evenly distributed around the circumference.

14. The stent of claim 13 wherein the stent includes 2×N struts between two adjacent bridges connecting two adjacent loops, wherein N is an odd integer.

15. The stent of claim 14 wherein
 four or more free cusps are disposed on both a first loop and a second loop between any two bridges connecting the first loop to the second loop,
 and
 in the non-expanded state, two or more gaps formed between facing cusps of the at least four free cusps align and at least two gaps formed between facing cusps of the at least four free cusps skew.

16. The stent of claim 15 wherein a plurality of radiopaque markers are distributed around a circumference of the stent, each of the radiopaque markers positioned in a recess defined between outer surfaces of adjacent end cusps.

17. The stent of claim 13 wherein the stent includes 2×N struts between two adjacent bridges connecting two adjacent loops, wherein N is an even integer.

18. The stent of claim 17 wherein
 four or more free cusps are disposed on both a first loop and a second loop between any two bridges connecting the first loop to the second loop,
 and
 in the non-expanded state, two or more gaps formed between facing cusps of the at least four free cusps align and at least two gaps formed between facing cusps of the at least four free cusps skew.

19. The stent of claim 18 wherein a plurality of radiopaque markers are distributed around a circumference of the stent, each of the radiopaque markers positioned in a recess defined between outer surfaces of adjacent end cusps.

* * * * *